United States Patent
Kuusela et al.

(10) Patent No.: US 10,653,893 B2
(45) Date of Patent: May 19, 2020

(54) RADIATION TREATMENT BASED UPON USER SPECIFICATION OF AT LEAST ONE CUSTOM DVH ESTIMATION MODEL TRAINING FEATURE

(71) Applicant: Varian Medical Systems International AG, Cham (CH)

(72) Inventors: Esa Kuusela, Espoo (FI); Maria Cordero Marcos, Espoo (FI); Hannu Laaksonen, Espoo (FI)

(73) Assignee: Varian Medical Systems International AG, Steinhausen (CH)

( * ) Notice: Subject to any disclaimer, the term of this patent is extended or adjusted under 35 U.S.C. 154(b) by 268 days.

(21) Appl. No.: 15/690,525

(22) Filed: Aug. 30, 2017

(65) Prior Publication Data

US 2019/0060671 A1    Feb. 28, 2019

(51) Int. Cl.
*A61N 5/10* (2006.01)

(52) U.S. Cl.
CPC ......... *A61N 5/1048* (2013.01); *A61N 5/1031* (2013.01); *A61N 2005/1074* (2013.01)

(58) Field of Classification Search
CPC .............. A61N 5/103–1039; A61N 2005/1041
See application file for complete search history.

(56) References Cited

U.S. PATENT DOCUMENTS

| | | | | |
|---|---|---|---|---|
| 2012/0310615 A1* | 12/2012 | Moore | ................ | G06F 19/3481 703/11 |
| 2014/0350863 A1* | 11/2014 | Hartman | .............. | A61N 5/1031 702/19 |
| 2015/0094519 A1* | 4/2015 | Kuusela | ............... | A61N 5/1039 600/1 |
| 2016/0129282 A1* | 5/2016 | Yin | ........................ | A61N 5/103 600/1 |
| 2018/0043182 A1* | 2/2018 | Wu | ........................ | G06Q 50/24 |
| 2019/0192880 A1* | 6/2019 | Hibbard | ............... | A61N 5/1031 |

* cited by examiner

*Primary Examiner* — Thaddeus B Cox
(74) *Attorney, Agent, or Firm* — Fitch, Even, Tabin & Flannery LLP

(57) ABSTRACT

A control circuit provides an opportunity via a user interface for a user to specify at least one custom DVH estimation model training feature. The control circuit then combines a predetermined set of DVH estimation model training features with a user-specified customer DVH estimation model training feature to provide a combined feature set. The control circuit uses the combined feature set to train a knowledge-based DVH estimation model which is then used to provide a DVH estimation for use when developing/optimizing a radiation treatment plan. That resultant radiation treatment plan then controls a radiation-administration platform to provide a therapeutic radiation dose to a patient.

19 Claims, 3 Drawing Sheets

US 10,653,893 B2

RADIATION TREATMENT BASED UPON USER SPECIFICATION OF AT LEAST ONE CUSTOM DVH ESTIMATION MODEL TRAINING FEATURE

TECHNICAL FIELD

These teachings relate generally to the use of radiation as a therapeutic treatment and more specifically to the formation and use of corresponding radiation-treatment plans.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not inherently discriminate between unwanted areas and adjacent healthy tissues, organs, or the like that are desired or even critical to continued survival of the patient. As a result, radiation is ordinarily applied in a carefully administered manner to at least attempt to restrict the radiation to a given target volume.

Treatment plans typically serve to specify any number of operating parameters as pertain to the administration of such treatment with respect to a given patient by use of a given radiation-treatment platform. Such treatment plans are often optimized prior to use. (As used herein, "optimization" will be understood to refer to improving upon a candidate treatment plan without necessarily ensuring that the optimized result is, in fact, the singular best solution.) Many optimization approaches use an automated incremental methodology where various optimization results are calculated and tested in turn using a variety of automatically-modified (i.e., "incremented") treatment plan optimization parameters.

It is not untypical to employ a dose volume histogram (DVH) estimation when optimizing a radiation treatment plan. The DVH estimation, in turn, is sometimes provided by use of a DVH estimation model. DVH estimation models themselves typically make use of a set of DVH estimation model training features. For example, when the plan requires minimizing radiation exposure to a particular so-called organ at risk, one or more parameters that serve to represent or characterize that organ at risk can serve as such training features. Existing practice tends to require numerous instances where a particular organ at risk structure has been previously characterized to thereby hopefully ensure an accurate model in those regards. Unfortunately, for certain treatment types (for example, using a specific field geometry setting), creating a DVH estimation model for a certain organ at risk may not be able to efficiently and/or effectively utilize a previously-defined set of DVH estimation model training features. For example, even though one might be able to train a good model for all organs typically involved in head-and-neck treatments or prostate treatments, a current set of predefined features nevertheless might not allow a good model to be trained for ribs in a lung-SBRT (Stereotactic Body Radiation Therapy) treatment.

BRIEF DESCRIPTION OF THE DRAWINGS

The above needs are at least partially met through provision of the radiation treatment based upon user specification of at least one custom DVH estimation model training feature described in the following detailed description, particularly when studied in conjunction with the drawings, wherein.

Figure 1:
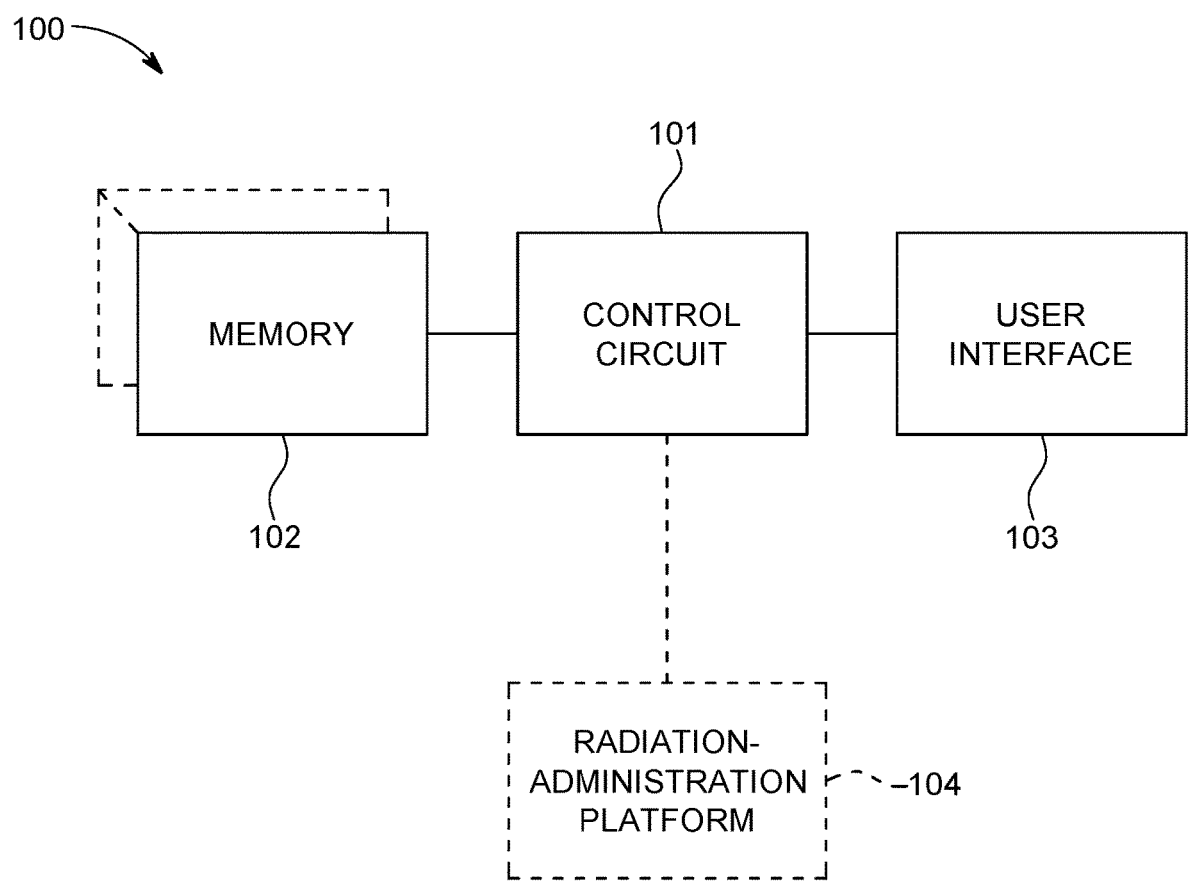
FIG. 1 comprises a block diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments a control circuit provides an opportunity via a user interface for a user to specify at least one custom DVH estimation model training feature. The control circuit then combines a predetermined set of DVH estimation model training features with a user-specified customer DVH estimation model training feature to provide a combined feature set. The control circuit uses the combined feature set to train a knowledge-based DVH estimation model which is then used to provide a DVH estimation for use when developing/optimizing a radiation treatment plan. That resultant radiation treatment plan then controls a radiation-administration platform to provide a therapeutic radiation dose to a patient.

By one approach the aforementioned opportunity to specify the at least one custom DVH estimation model training feature comprises a scripting-based opportunity. The custom DVH estimation model training feature may itself constitute, for example, a new model statistic (such as a statistic regarding a distance) or a radiation beam metric.

By one approach, these teachings will further accommodate using substitute tissue information as a basis for training the knowledge-based DVH estimation model instead of organ at risk information. The foregoing may comprise, for example, selectively avoiding tissue that includes bone or that specifically includes bone as desired. By one approach the substitute tissue information corresponds to substitute tissue that is within a predetermined degree of similarity to density of the organ at risk.

These teachings are well designed to address cases where a predefined set of available features do not well describe the relevant geometrical variation presented by a given organ-at-risk in the context of a certain treatment type by allowing the user to augment the feature set. By one approach these user-selected features are available for consideration by the optimization algorithm as possible parameterizations to be used with a particular corresponding model. These teachings are also useful to help provide useful results in situations where a model for a particular organ at risk structure is either unavailable or not yet trustworthy through experience.

These and other benefits may become clearer upon making a thorough review and study of the following detailed description. Referring now to the drawings, and in particular to FIG. 1, an illustrative apparatus 100 that is compatible with many of these teachings will now be presented.

In this particular example, the enabling apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). In addition, the control circuit 101 can constitute an integral entity or can comprise a plurality of distributed entities. These architectural options for such structures are well known and understood in the art and require no further description here. This control circuit 101 is configured (for example, by using corresponding programming as will be well understood by those skilled in the art) to carry out one or more of the steps, actions, and/or functions described herein.

By one optional approach the control circuit 101 operably couples to a memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to radiation treatment plan information, radiation treatment plan optimization information, and a predetermined set of dose volume histogram estimation model training features as described herein, this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM).)

If desired, the control circuit 101 can optionally operably couples to a network interface (not shown). So configured the control circuit can communicate with other elements (both within the apparatus and external thereto) via the network interface. Network interfaces, including both wireless and non-wireless platforms, are well understood in the art and require no particular elaboration here.

In this illustrative example the control circuit 101 operably couples to a user interface 103. This user interface 103 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user. For the sake of an illustrative example, but without intending any particular limitations in these regards, it will be presumed here that the user interface 103 at least comprises a touch-screen display.

These teachings will also optionally accommodate operably coupling the control circuit 101 to a radiation-administration platform 104. Generally speaking, a radiation-administration platform comprises an apparatus configured to administer a controlled dose of high-energy radiation (such as x-rays) to a target volume in a patient. The x-ray source can comprise, for example, a radio-frequency (RF) linear particle accelerator-based (linac-based) x-ray source, such as the Varian Linatron M9. The linac is a type of particle accelerator that greatly increases the kinetic energy of charged subatomic particles or ions by subjecting the charged particles to a series of oscillating electric potentials along a linear beamline, which can be used to generate ionizing radiation (e.g., X-rays) and high energy electrons. The radiation source may itself be selectively movable (for example, along an arc that partially or fully circumscribes the patient) during administration of the radiation treatment.

In a typical application setting the radiation-administration platform will also include, in addition to the radiation source, one or more beam shaping components such as but not limited to jaw/collimators, multi-leaf collimators, and so forth. The radiation-administration platform may also include a patient support surface such as but not limited to a so-called couch (which may or may not itself be selectively moveable during the treatment session). Depending upon the application setting, these components may be directly controlled by the control circuit 101 or may only be indirectly controlled thereby (for example, when the radiation-administration platform 104 includes its own control circuit that receives the radiation-treatment plan information from the aforementioned control circuit 101).

Figure 2:
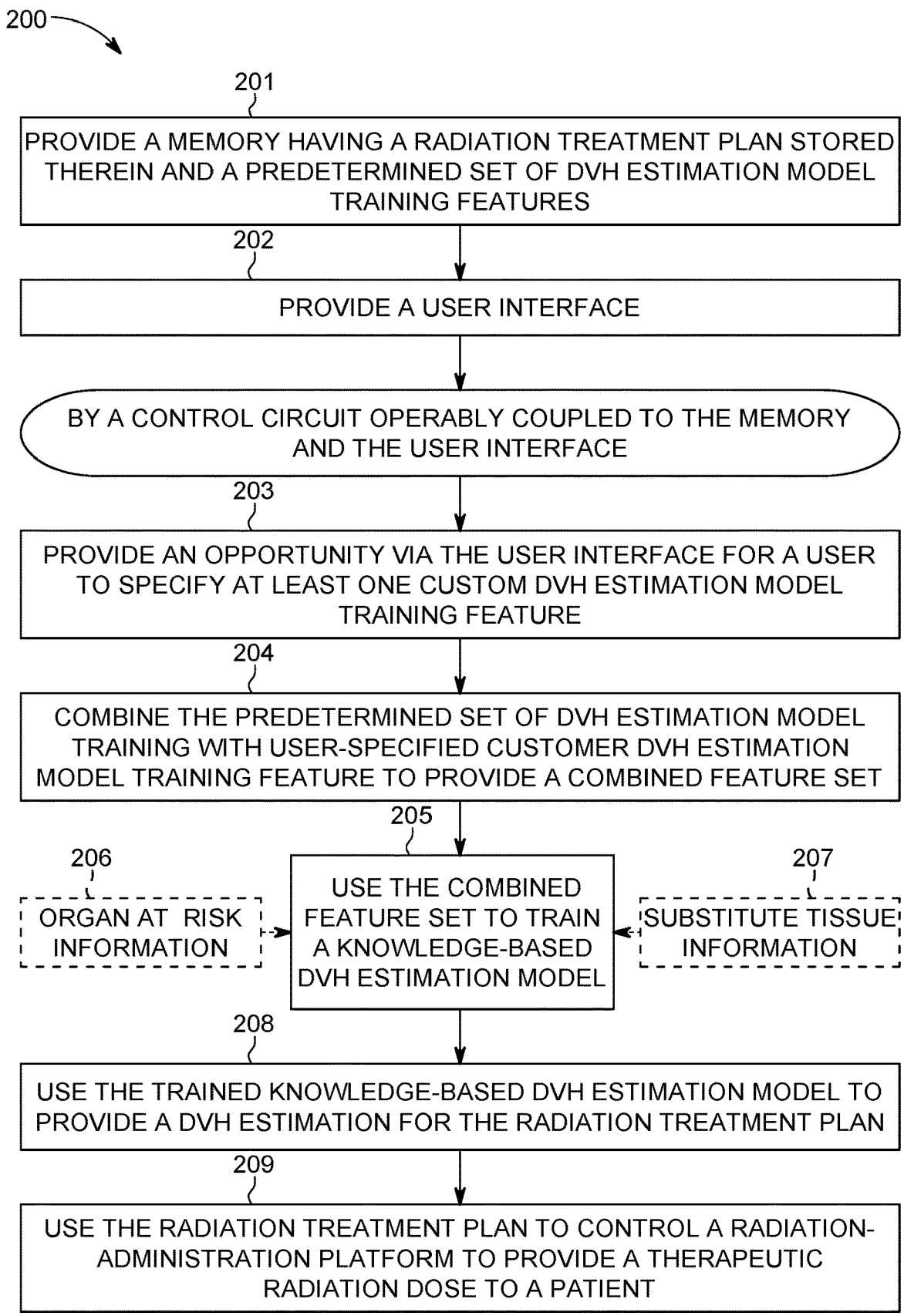
FIG. 2 comprises a flow diagram as configured in accordance with various embodiments of these teachings.

Referring now to FIG. 2, a corresponding process 200 will be described. At block 201 this process 200 provides a memory 102 (as described above) having at least one radiation treatment plan stored therein along with a predetermined set of dose volume histogram (DVH) estimation model training features.

DVH's typically represent three-dimensional dose distributions in a graphical two-dimensional format (the three-dimensional dose distributions being created, for example, in a computerized radiation-treatment planning system based on a three-dimensional reconstruction of an X-ray computed tomography scan and study). The "volume" referred to in DVH analysis can be, for example, the radiation-treatment target, a healthy organ located near such a target, an arbitrary structure, and so forth.

DVH's are often visualized in either of two ways: as differential DVH's or as cumulative DVH's. With differential DVH's the column height for a given dose bin corresponds to the volume of the structure that receives that dose. Bin doses typically extend along the horizontal axis while structure volumes (either percent or absolute volumes) extend along the vertical axis.

A cumulative DVH is typically plotted with bin doses along the horizontal axis but has a column height for the first bin that represents the volume of structure(s) that receive greater than or equal to that dose. The column height of the second bin then represents the volume of structure(s) that receive greater than or equal to that dose, and so forth. With high granularity a cumulative DVH often appears as a smooth line graph. For many application settings cumulative DVH's are preferred over differential DVH's but this process 200 can accommodate either approach.

Figure 3:
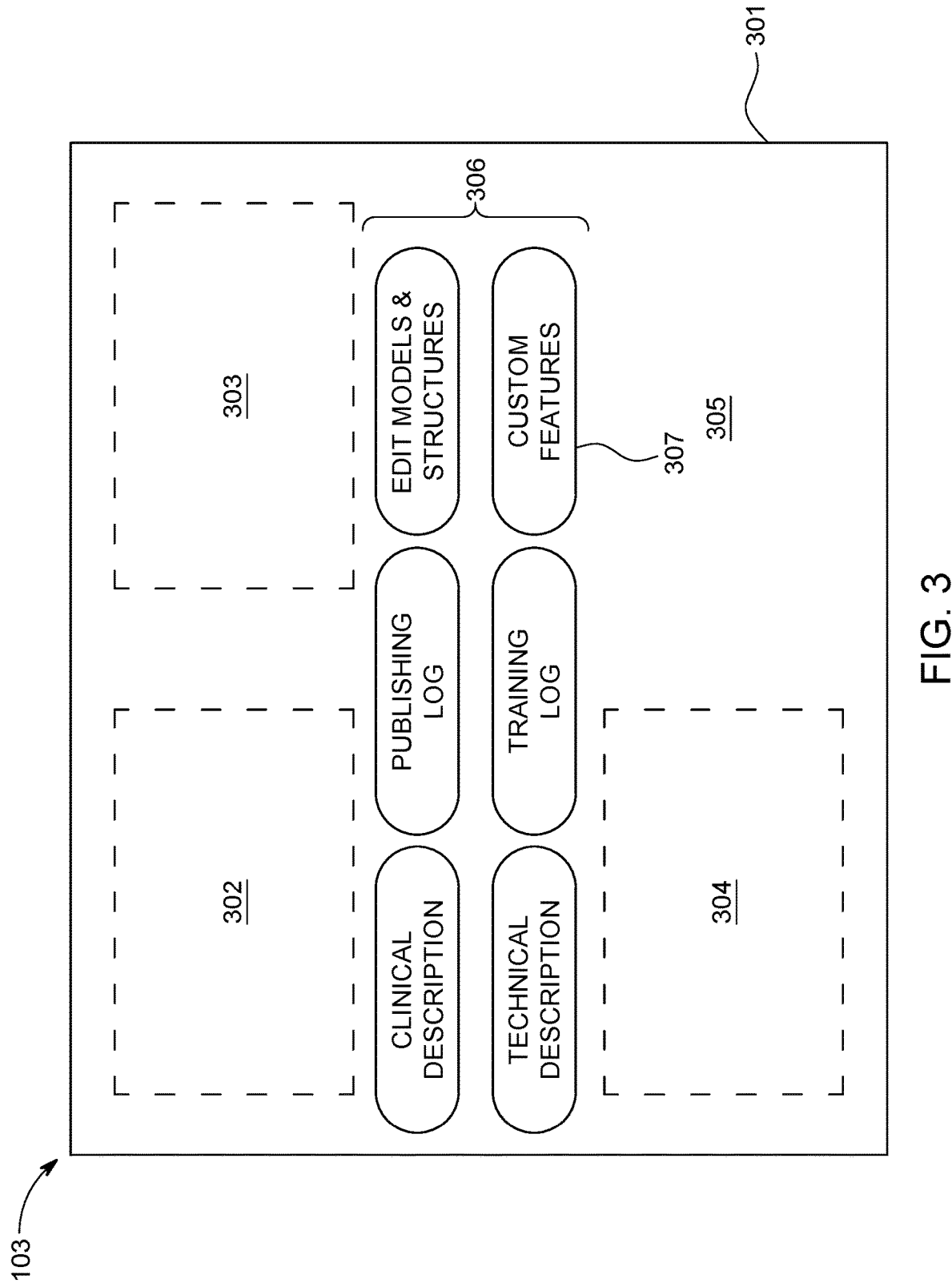
FIG. 3 comprises a user interface screenshot as configured in accordance with various embodiments of these teachings.

At block 202 this process also provides the aforementioned user interface 103. As noted above, for the purpose of this description but without intending any particular limitations it will be presumed here that this user interface 103 comprises, at least in part, a touch-screen interface. FIG. 3 provides an illustrative example in these regards. In this example the touch-screen display 301 of the touch-stream interface parses the available display area to accommodate different categories of information and/or controls.

A first area, denoted by reference numeral 302, can present textual information regarding an identifier for a selected model, a version number for the selected model, an identification of the relevant anatomical region, an indication or certification regarding whether the model has been trained and/or published, a textual description pertaining to the model, a date identifying when the model was last modified, and so forth.

A second area, denoted by reference numeral 303, can present selectable plans corresponding to the DVH estimation model. This information can include, for example, patient ID information, course ID information, plan ID information, plan prescription information, structure matching information, and so forth.

A third area, denoted by reference numeral 304, can present information regarding model structures and objective, normal tissue objectives, smoothing parameters (corresponding to Intensity-Modulated Radiation Therapy (IMRT), and so forth.

A fourth area, denoted by reference numeral 305, can present a two-dimensional graphic depiction of a corresponding DVH plot, and can include opportunities for the user to select from amongst a plurality of different such plots.

And a fifth area, denoted by reference numeral 306, can provide a plurality of user-assertable buttons to bring up various assorted information balloons, sub-menus, functions, and/or features as desired.

It is also presumed for the sake of this description that the remaining steps of this process 200 are carried out by the aforementioned control circuit 101 that operably couples to the aforementioned memory 102 and user interface 103 (as well as, optionally, the aforementioned radiation-administration platform 104).

At block 203 the control circuit 101 provides an opportunity via the user interface 103 for a user (such as a physician or certified medical technician) to specify at least one custom DVH estimation model training feature. Referring momentarily to FIG. 3, in this example this opportunity may comprise a user-assertable button 307 that brings up at least one custom feature, where that custom feature comprises the aforementioned custom DVH estimation model training feature. In this example it will be presumed that asserting this custom features button 307 will bring up a scripting-based opportunity. So configured, the user can readily provide a script file that, upon being run, converts input data into a corresponding set of features that are then provided as additional information to the model training algorithms utilized by the control circuit 101.

By one approach, the foregoing comprises providing an opportunity to specify a new model statistic for the DVH estimation model. For example, the new model statistic can comprise a statistic regarding a distance. Examples of useful distances include but are not limited to distances regarding various geometrical features such as a length, width, or depth of a target volume or organ-at-risk, a distance comprising a relative distance between a target volume or an organ-at-risk and some other structure or point(s) of interest, and so forth.

By another approach, in lieu of the foregoing or in combination therewith, the foregoing may comprise an opportunity to specify a radiation beam metric such as, but not limited to, a weighted geometric metric for a corresponding radiation beam direction.

And as yet another approach, and again in lieu of the foregoing or in combination therewith, the foregoing opportunity may comprise an opportunity to specify at least one physical difference between an application setting to be modeled and a given reference application setting. Other possibilities can of course be accommodated as desired.

At block 204 the control circuit combines the predetermined set of DVH estimation model training features provided by the memory 102 with the user-specified customer DVH estimation model training feature (or features) to provide a resultant combined feature set. (It may be noted that, by one approach, this user-based opportunity constitutes an opportunity to add to an existing feature set but not to edit or change one of the already-existing features in the set.) Accordingly, the resultant combined feature set includes both non-user-specified DVH estimation model training features along with at least one user-specified DVH estimation model training feature.

At block 205 the control circuit 101 then uses that combined feature set to train a knowledge-based DVH estimation model. Generally speaking, there are various known approaches to training a knowledge-based DVH estimation model using a feature set and the present teachings are not overly sensitive to any particular selections in these regards. That said, many typical approaches in these regards make use of previously developed and verified organ-at-risk information 206. It is not always the case, however, that such information 206 is available or, if available, sufficiently trustworthy.

To accommodate such a situation this process 200 will optionally provide for using substitute tissue information 207 as a basis for training the knowledge-based DVH estimation model instead of organ-at-risk information 206. In particular, this substitute tissue information can correspond to any tissue other than the tissue that comprises the particular organ at risk (as versus the target volume). Examples include tissue that is normal ("normal" in that the tissue is not subject to any disease process or other external stress factor). These teachings are generally open to a variety of such tissues including, for example, muscle tissue and a variety of organs.

By one approach the substitute tissue should be within a predetermined degree of similarity to the density of the organ at risk (where that density can represent a particular part of the organ at risk or, for example an average or mean density for the organ at risk). For example, it may be required that the substitute tissue be within one percent, two percent, five percent, ten percent, fifteen percent, or some other percentage of choice of the organ-at-risk's density.

These teachings will accommodate other vetting requirements, in lieu of the foregoing or in combination therewith, if desired. For example, the substitute tissue selection criteria may require that the substitute tissue include bone (when, for example, the organ-at-risk includes bone) or, conversely, may require that the substitute tissue include no bone (when, for example, the organ-at-risk is less dense than bone) such that the selection process selectively avoids, or includes, tissue that includes bone, respectively.

Using an appropriately selected model for substitute tissue can serve as a useful and available model that can adequately serve, at least in many instances, in lieu of a model for structures that lack sufficient antecedent data.

At block 208 the control circuit 101 uses the trained knowledge-based DVH estimation model to provide a DVH estimation for the radiation treatment plan (which is to say that the DVH estimation is utilized as a guiding parameter/criteria/goal when optimizing a resultant radiation treatment plan). At block 209 that radiation treatment plan is then used to control a radiation administration platform 104 to provide a therapeutic radiation dose to the patient. These steps are well understood in the art and require no further elaboration here.

So configured, these teachings permit a user to proceed with generally understood and available radiation treatment plan optimization techniques even when the provided set of predefined features do not fully or adequately describe the relevant geometric variations that characterize a particular application setting (i.e., when the available algorithms cannot configure a well-behaving model that explains certain variations in the calculated outcomes). The teachings provided herein permit a user to suggest their own features in these regards to be considered by the algorithm as possible parameterizations. By one approach these suggestions may be limited to use with only a particular specified model.

Generally speaking, DVH estimation model training algorithms receive as input structure sets, field geometry information, and outcome dose specifications for each of a plurality of patient cases in a model training set. A predefined set of geometrical features are used as candidate independent parameters. These teachings permit the model definition to also include the user-provided information (expressed, for example, as a script file) that converts such input data into a set of features that have been provided as additional information to the model training algorithm.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. An apparatus comprising:
a memory having a radiation treatment plan stored therein and a predetermined set of dose volume histogram (DVH) estimation model training features;
a user interface;
a control circuit operably coupled to the memory and the user interface and configured to:
provide an opportunity via the user interface for a user to specify at least one custom DVH estimation model training feature;
combine the predetermined set of DVH estimation model training features with a user-specified custom DVH estimation model training feature to provide a combined feature set;
use the combined feature set to train a knowledge-based DVH estimation model;
use the trained knowledge-based DVH estimation model to provide a DVH estimation for the radiation treatment plan;
use the radiation treatment plan to control a radiation-administration platform to provide a therapeutic radiation dose to a patient.

2. The apparatus of claim 1 wherein the control circuit is configured to provide the opportunity to specify the at least one custom DVH estimation model training feature via a scripting-based opportunity.

3. The apparatus of claim 1 wherein the control circuit is configured to provide the opportunity to specify the at least one custom DVH estimation model training feature by providing an opportunity to specify a new model statistic.

4. The apparatus of claim 3 wherein the new model statistic comprises a statistic regarding a distance.

5. The apparatus of claim 1 wherein the control circuit is configured to provide the opportunity to specify the at least one custom DVH estimation model training feature by providing an opportunity to specify a radiation beam metric.

6. The apparatus of claim 5 wherein the radiation beam metric comprises a weighted geometric metric for a corresponding radiation beam direction.

7. The apparatus of claim 1 wherein the control circuit is configured to provide the opportunity to specify the at least one custom DVH estimation model training feature by providing an opportunity to specify at least one physical difference between an application setting to be modeled and a given reference application setting.

8. The apparatus of claim 1 wherein the control circuit is further configured to:
use substitute tissue information as a basis for training the knowledge-based DVH estimation model instead of organ at risk (OAR) information.

9. The apparatus of claim 8 wherein the control circuit is configured to use substitute tissue information by selectively avoiding tissue that includes bone.

10. The apparatus of claim 8 wherein the control circuit is configured to use substitute tissue information by selectively including tissue that includes bone.

11. The apparatus of claim 8 wherein the substitute tissue information corresponds to substitute tissue that is within a predetermined degree of similarity to density of the OAR.

12. A method comprising:
providing a memory having a radiation treatment plan stored therein and a predetermined set of dose volume histogram (DVH) estimation model training features;
providing a user interface;
by a control circuit operably coupled to the memory and the user interface:
providing an opportunity via the user interface for a user to specify at least one custom DVH estimation model training feature;
combining the predetermined set of DVH estimation model training features with a user-specified custom DVH estimation model training feature to provide a combined feature set;
using the combined feature set to train a knowledge-based DVH estimation model; using the trained knowledge-based DVH estimation model to provide a DVH estimation for the radiation treatment plan;
using the radiation treatment plan to control a radiation-administration platform to provide a therapeutic radiation dose to a patient.

13. The method of claim 12 wherein providing the opportunity to specify the at least one custom DVH estimation model training feature comprises using a scripting-based opportunity.

14. The method of claim 12 wherein providing the opportunity to specify the at least one custom DVH estimation model training feature comprises providing an opportunity to specify a new model statistic.

15. The method of claim 14 wherein the new model statistic comprises a statistic regarding a distance.

16. The method of claim 12 wherein providing the opportunity to specify the at least one custom DVH estimation model training feature comprises providing an opportunity to specify a radiation beam metric.

17. The method of claim 16 wherein the radiation beam metric comprises a weighted geometric metric for a corresponding radiation beam direction.

18. The method of claim 1 further comprising:
    using substitute tissue information as a basis for training the knowledge-based DVH estimation model instead of organ at risk (OAR) information.

19. The method of claim 18 wherein the substitute tissue information corresponds to substitute tissue that is within a predetermined degree of similarity to density of the OAR.

* * * * *